(12) United States Patent
Sugaya

(10) Patent No.: US 11,684,250 B2
(45) Date of Patent: Jun. 27, 2023

(54) ENDOSCOPE SYSTEM, AND LEAK DETECTION PROCESSING METHOD AND LEAK DETECTION PROCESSING APPARATUS FOR ENDOSCOPE

(71) Applicant: OLYMPUS CORPORATION, Tokyo (JP)

(72) Inventor: Michihiro Sugaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 867 days.

(21) Appl. No.: 16/564,035

(22) Filed: Sep. 9, 2019

(65) Prior Publication Data

US 2020/0000329 A1 Jan. 2, 2020

Related U.S. Application Data

(63) Continuation of application No. PCT/JP2017/033775, filed on Sep. 19, 2017.

(30) Foreign Application Priority Data

Mar. 9, 2017 (JP) .................. 2017-045066

(51) Int. Cl.
*A61L 2/00* (2006.01)
*B08B 7/04* (2006.01)
*B08B 3/00* (2006.01)
*A61B 1/12* (2006.01)
(Continued)

(52) U.S. Cl.
CPC .......... *A61B 1/121* (2013.01); *A61B 1/00057* (2013.01); *A61B 1/00068* (2013.01); *A61B 1/00121* (2013.01); *A61B 90/70* (2016.02); *A61B 2090/701* (2016.02); *A61L 2202/24* (2013.01)

(58) Field of Classification Search
CPC ..... A61L 2/16; A61L 2/18; A61L 2/20; A61L 2202/24; A61B 1/121; A61B 1/00121; B08B 9/00; B08B 3/00
USPC ....... 422/1, 28, 292, 300; 134/18, 166, 56 R
See application file for complete search history.

(56) References Cited

U.S. PATENT DOCUMENTS

2007/0193605 A1* 8/2007 Kuroshima ............... A61L 2/24
134/166 R
2014/0166059 A1 6/2014 Kosugi et al.
2017/0027420 A1 2/2017 Choi et al.

FOREIGN PATENT DOCUMENTS

CN 103796572 A 5/2014
CN 106164639 A 11/2016
(Continued)

OTHER PUBLICATIONS

International Search Report dated Dec. 26, 2017 issued in PCT/JP2017/033775.

*Primary Examiner* — Monzer R Chorbaji
(74) *Attorney, Agent, or Firm* — Scully, Scott, Murphy & Presser, P.C.

(57) ABSTRACT

An endoscope system includes a valve configured to keep an internal space of an endoscope airtight, an air pump configured to open and close the valve by applying a negative pressure and a positive pressure, a pressure sensor configured to detect a pressure at a time of the negative pressure and the positive pressure being applied, and a control section configured to receive a detection signal from the pressure sensor, and perform drive control of the air pump.

9 Claims, 13 Drawing Sheets

(51) Int. Cl.
*A61B 90/70* (2016.01)
*A61B 1/00* (2006.01)

(56) References Cited

FOREIGN PATENT DOCUMENTS

JP 5379446 B2 12/2013
JP 2015-029649 A 2/2015

* cited by examiner

ENDOSCOPE SYSTEM, AND LEAK DETECTION PROCESSING METHOD AND LEAK DETECTION PROCESSING APPARATUS FOR ENDOSCOPE

CROSS REFERENCE TO RELATED APPLICATION

This application is a continuation application of PCT/JP2017/033775 filed on Sep. 19, 2017 and claims benefit of Japanese Application No. 2017-045066 filed in Japan on Mar. 9, 2017, the entire contents of which are incorporated herein by this reference.

BACKGROUND OF THE INVENTION

1. Field of the Invention

The present invention relates to an endoscope system that performs water leakage detection at a time of cleaning and disinfecting an endoscope, and a leak detection processing method and a leak detection processing apparatus for the endoscope.

2. Description of the Related Art

An endoscope that is used for the purpose of examination, treatment in a body, or the like has filth attached not only to an outer surface of an insertion portion that is inserted into a body but also to an inside of a conduit such as a treatment instrument insertion channel Therefore, it is necessary to clean and disinfect not only the outer surface but also the inside of the conduit of the endoscope after use by an endoscope cleaning/disinfecting apparatus or the like after simple cleaning.

Some of such endoscope cleaning/disinfecting apparatuses are equipped with a function of performing so-called water leakage detection processing for fear that water might enter the internal space of an endoscope and cause failure if a hole occurs in an outer sheath portion of a flexible tube or bending tube of the endoscope, or a conduit.

In the water leakage detection processing, as disclosed in Japanese Patent Application Laid-Open Publication No. 2015-29649, for example, a water leakage detecting pipe sleeve that communicates with an inside of an endoscope, and a water leakage detecting connector that communicates with an air-feeding portion of an endoscope cleaning/disinfecting apparatus are connected via a water leakage detecting tube.

Note that the water leakage detecting connector or the like has a check valve structure or the like having a valve that is urged to a closed state at a disconnected time in order to prevent entry of water into the inside.

Water leakage detection is performed by a method that measures a pressure change of a hermetically closed space inside the endoscope that is formed of the inside of the endoscope, water leakage detecting piping and the like after gas such as air is fed to the inside of the endoscope until the pressure inside the endoscope reaches a predetermined pressure from the air feeding portion of the endoscope cleaning/disinfecting apparatus, via the water leakage detecting connector and the water leakage detecting pipe sleeve.

SUMMARY OF THE INVENTION

An endoscope system in one aspect of the present invention includes a valve configured to keep an internal space of an endoscope airtight, a pipe sleeve configured to be connectable to a leak detection mechanism having the valve, an air-feeding and suction mechanism configured to open the valve by applying a negative pressure, close the valve by performing pressurization, and detach the pipe sleeve from the leak detection mechanism by continuing pressurization, in a state where the leak detection mechanism and the pipe sleeve are connected to each other, a pressure sensor configured to detect a pressure at a time of the negative pressure being applied, and output a first detection signal indicating that a hole does not occur in a member that forms the internal space of the endoscope, and a control section configured to perform drive control to the air-feeding and suction mechanism that applies the negative pressure, to perform pressurization by the first detection signal being inputted from the pressure sensor.

A leak detection processing method for an endoscope according to the endoscope system in one aspect of the present invention includes opening the valve provided in the leak detection mechanism that is connected to the pipe sleeve by applying the negative pressure via the pipe sleeve by driving the air-feeding and suction mechanism, applying the negative pressure for a predetermined time period, detecting a pressure inside of the endoscope by the pressure sensor, and closing the valve by performing pressurization by driving the air-feeding and suction mechanism, and detaching the pipe sleeve from the leak detection mechanism by continuing pressurization, when the first detection signal indicating that a hole does not occur in the member that forms the internal space of the endoscope is inputted from the sensor.

A leak detection processing apparatus in one aspect of the present invention includes an air-feeding and suction mechanism connected to an internal space of an endoscope, and configured to pressurize or decompress the internal space by air feeding or suction, and cut connection to the internal space by continuing pressurization, a pressure sensor configured to detect pressure in the internal space, and output a first detection signal indicating that a hole does not occur in the internal space, when a negative pressure is applied by the decompression of the air-feeding and suction mechanism, and a control section configured to perform drive operation to the air-feeding and suction mechanism that applies the negative pressure, to perform pressurization, in response to input of the first detection signal.

DETAILED DESCRIPTION OF THE PREFERRED EMBODIMENT(S)

Figure 1:
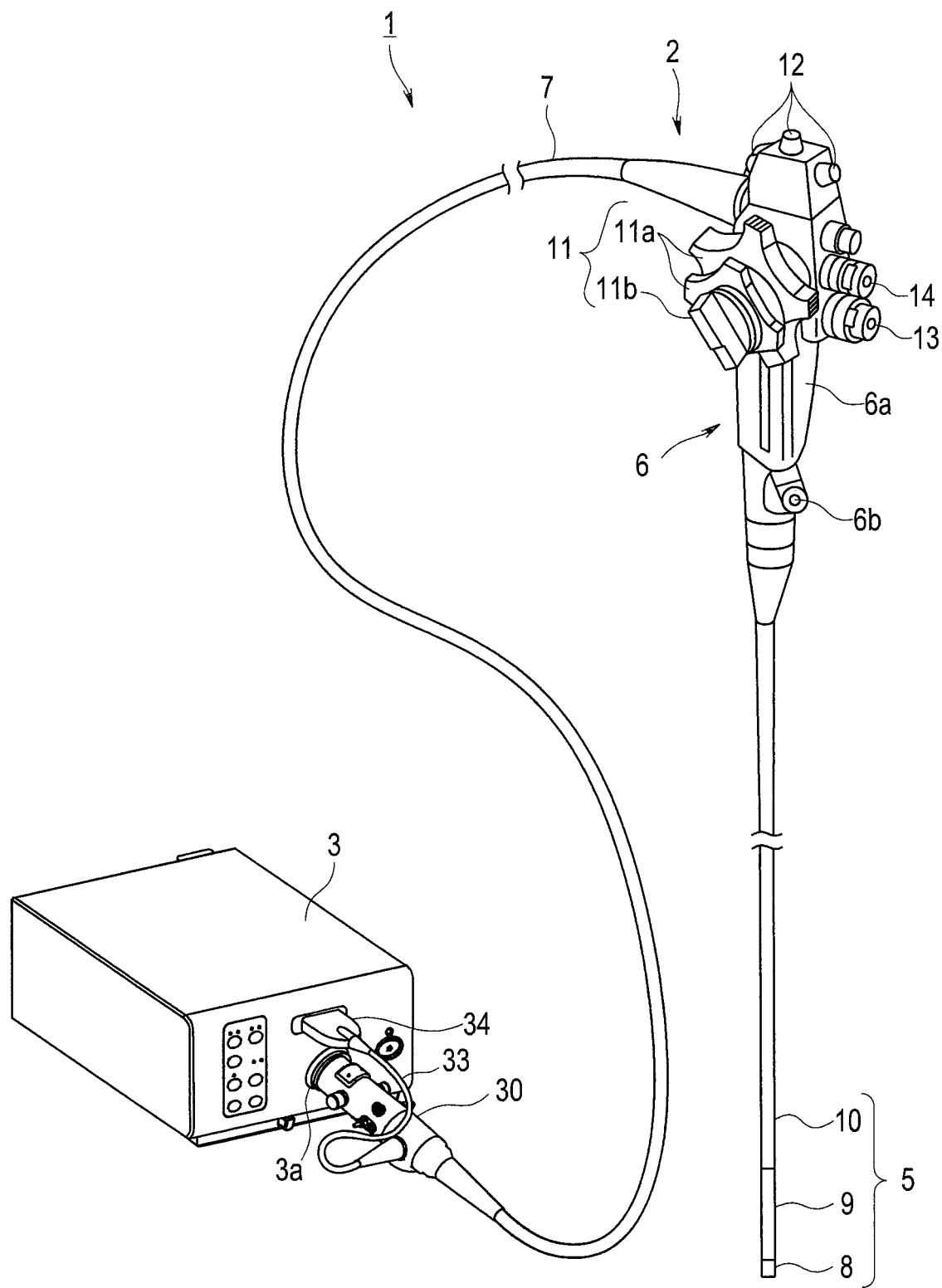
FIG. 1 is a general view illustrating a configuration of an endoscope apparatus.

A preferred embodiment of the present invention will be described below with reference to the drawings.

Note that in the drawings used for the following explanation, in order to make respective components have such sizes as to be recognizable in the drawings, scales are made to be different for each of the components, and the present invention is not limited to only quantities of the components, shapes of the components, ratios of the sizes of the components, and relative positional relationships of the respective components that are illustrated in the drawings. In the following explanation, the vertical direction viewed as one faces the sheet of the drawings is described as an upper part and a lower part of the component in some cases.

Figure 2:
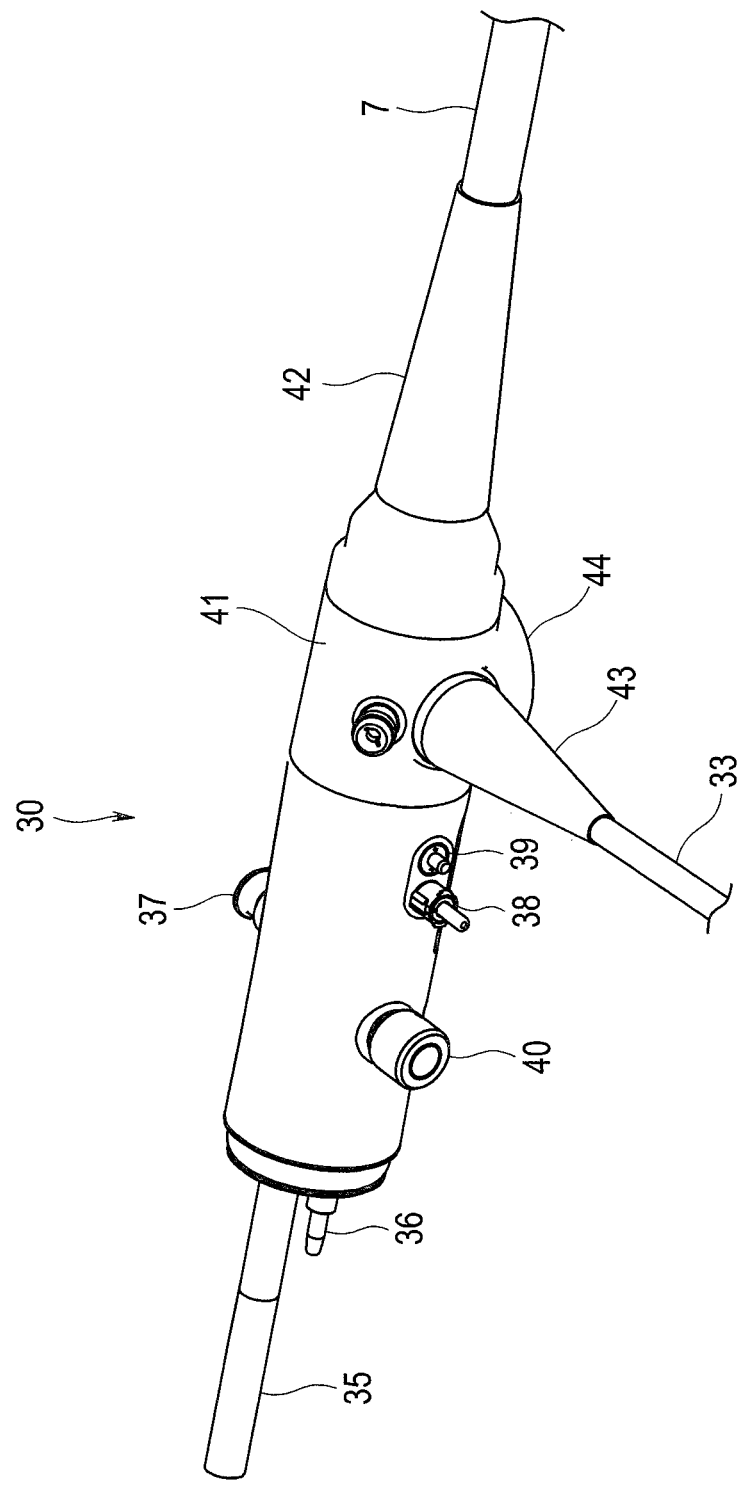
FIG. 2 is a perspective view illustrating an endoscope connector.
Figure 3:
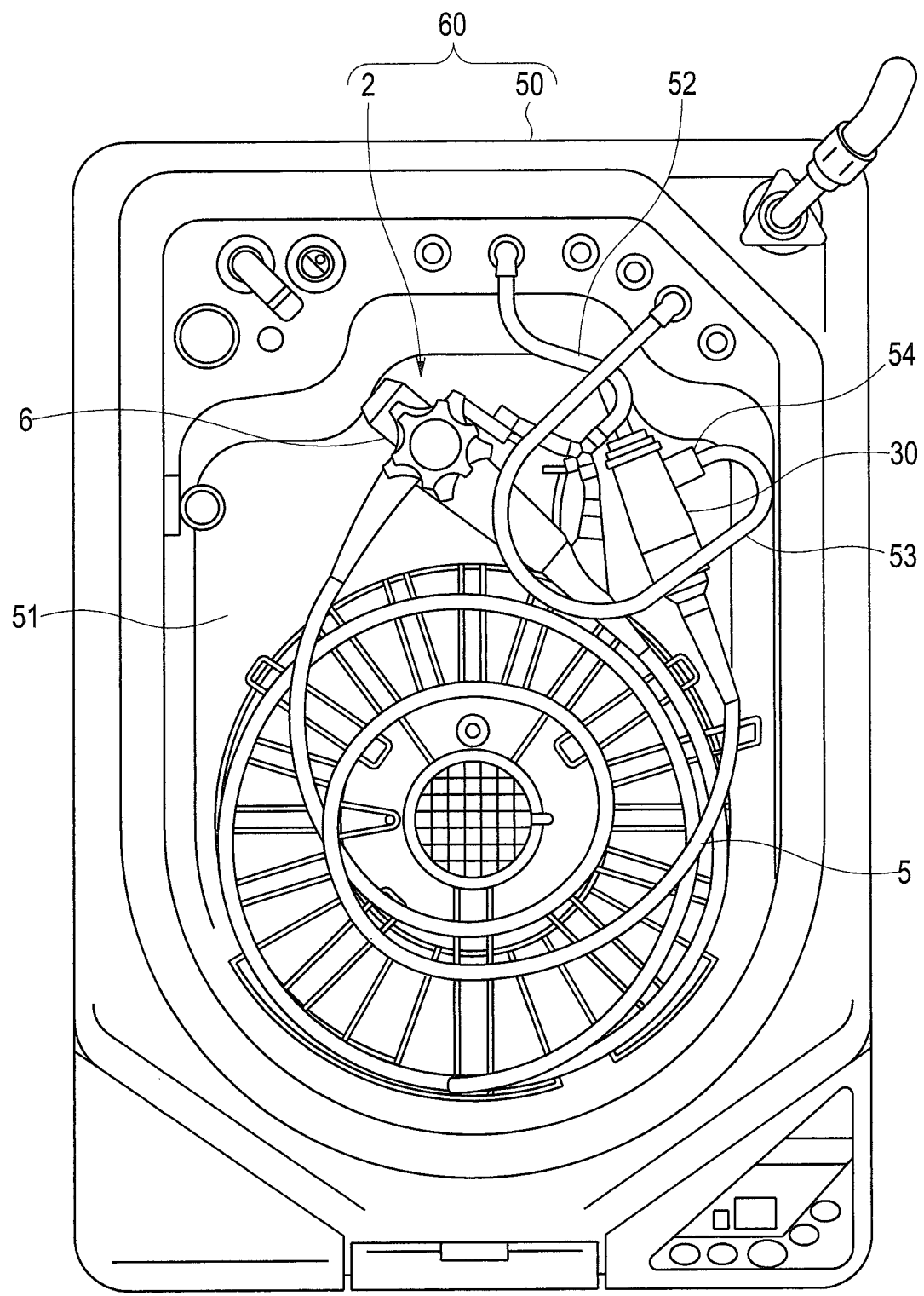
FIG. 3 is a plan view illustrating a state where an endoscope is set in a sink of an endoscope cleaning/disinfecting apparatus.
Figure 4:
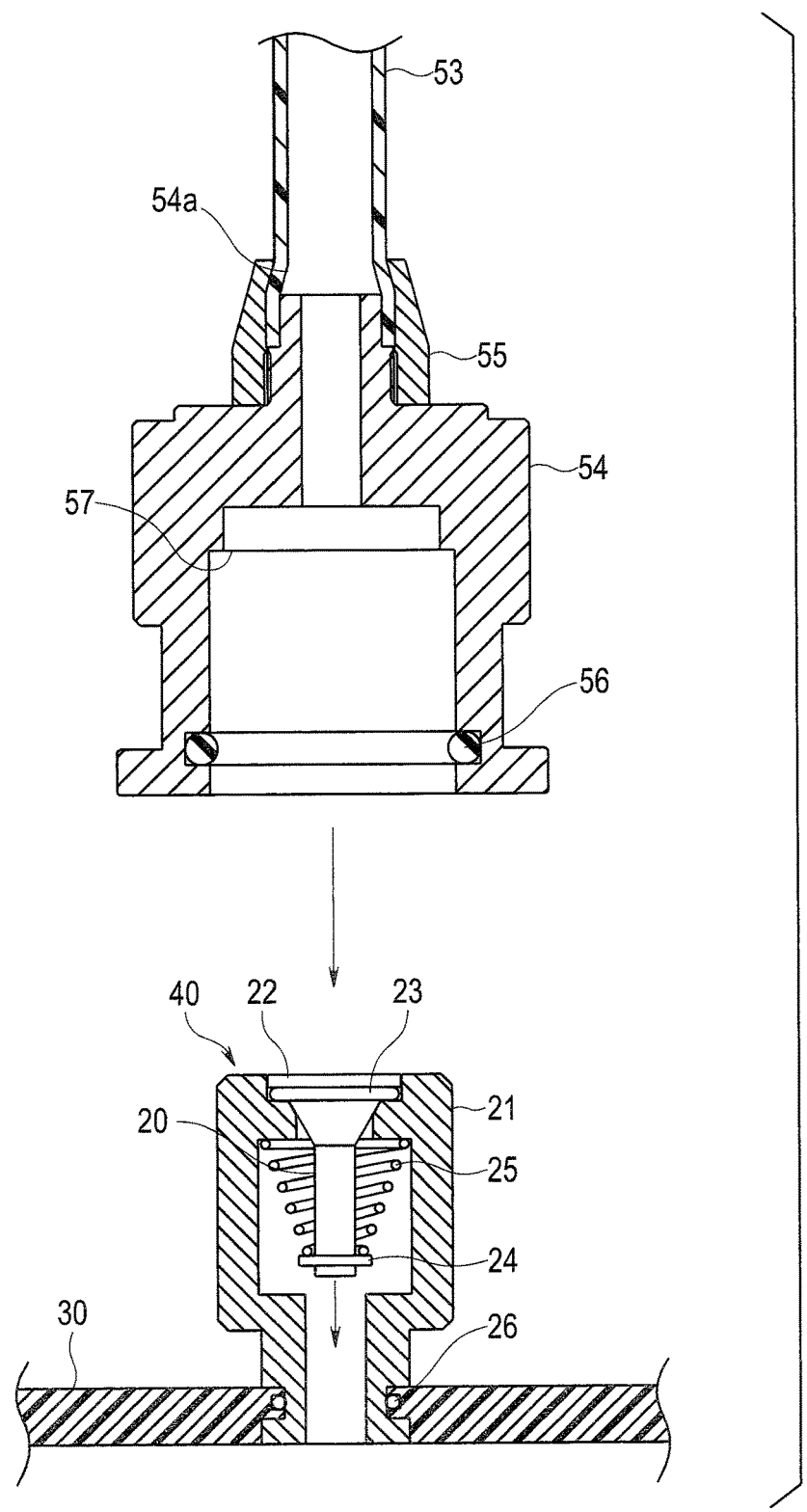
FIG. 4 is a sectional view illustrating configurations of a leak detection pipe sleeve and an air pipe sleeve.
Figure 5:
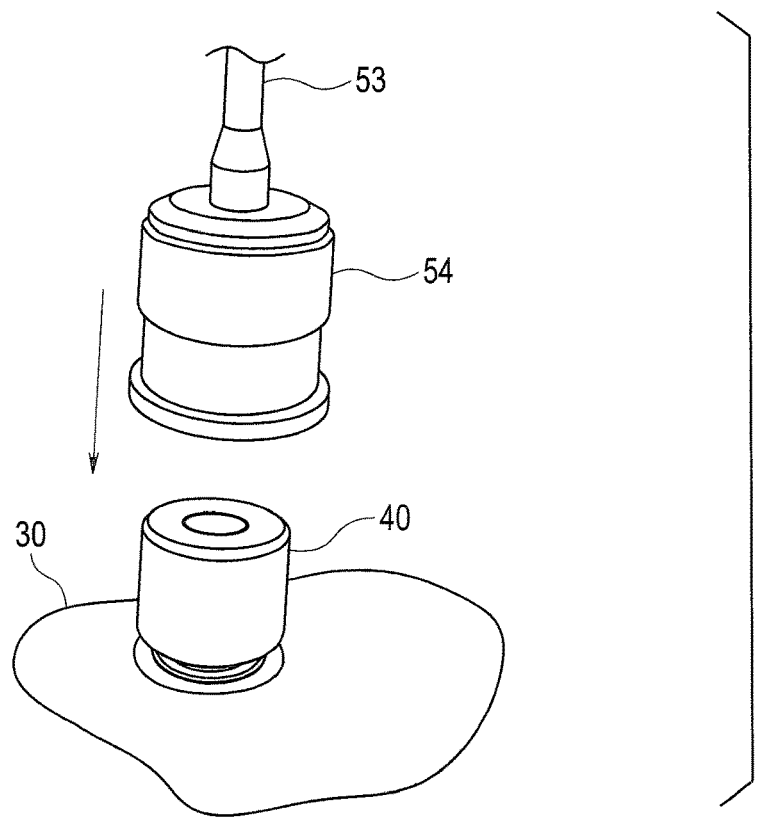
FIG. 5 is a perspective view illustrating a state where the air pipe sleeve is being connected to the leak detection pipe sleeve.
Figure 6:
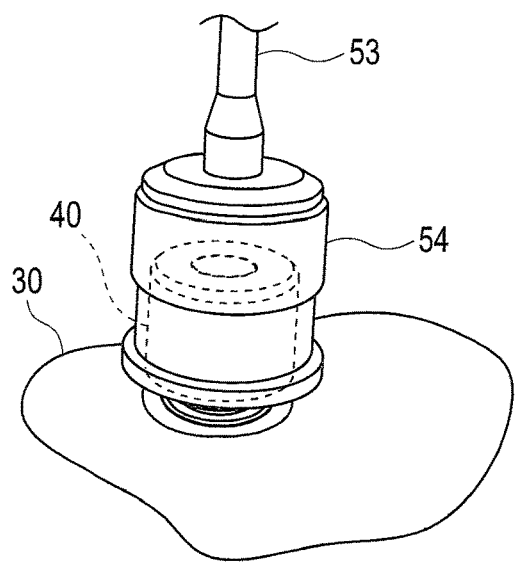
FIG. 6 is a perspective view illustrating a state where the air pipe sleeve is connected to the leak detection pipe sleeve.
Figure 7:
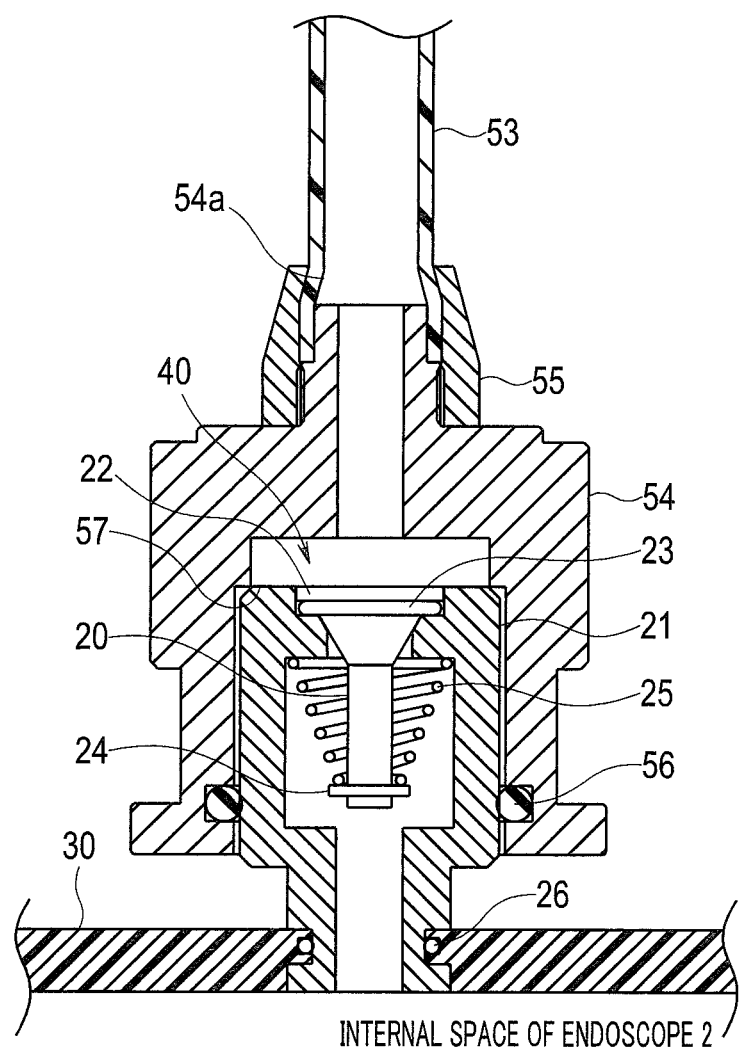
FIG. 7 is a sectional view illustrating the state where the air pipe sleeve is connected to the leak detection pipe sleeve.
Figure 8:
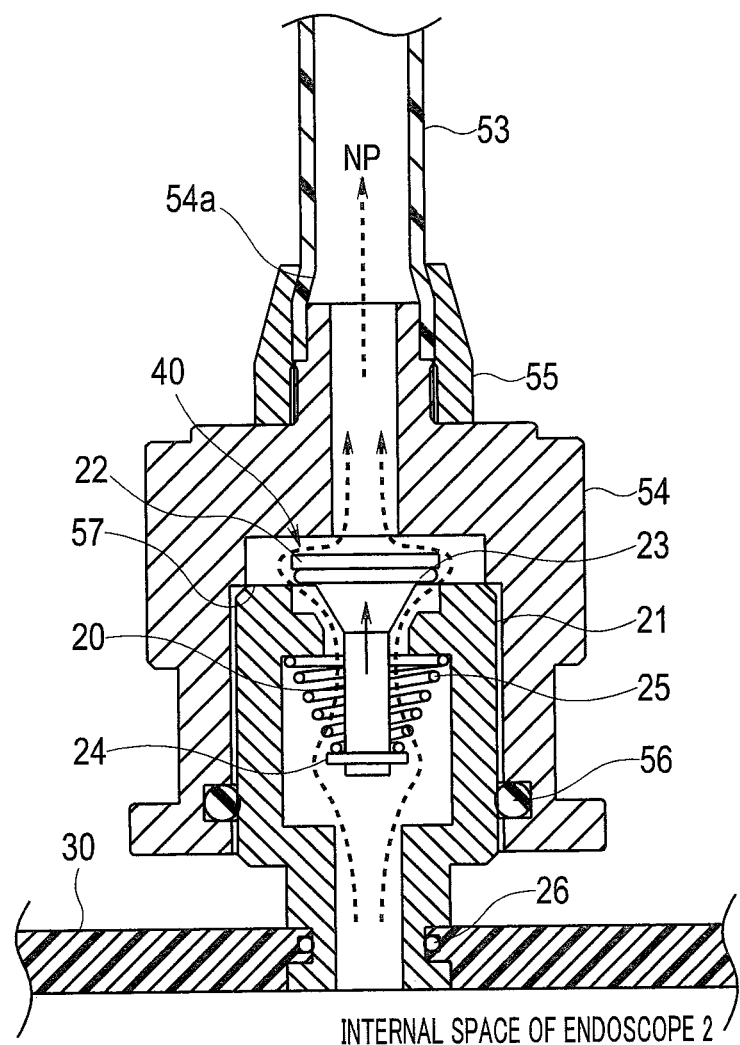
FIG. 8 is a sectional view illustrating a state where the air pipe sleeve is connected to the leak detection pipe sleeve, and a negative pressure is applied.
Figure 9:
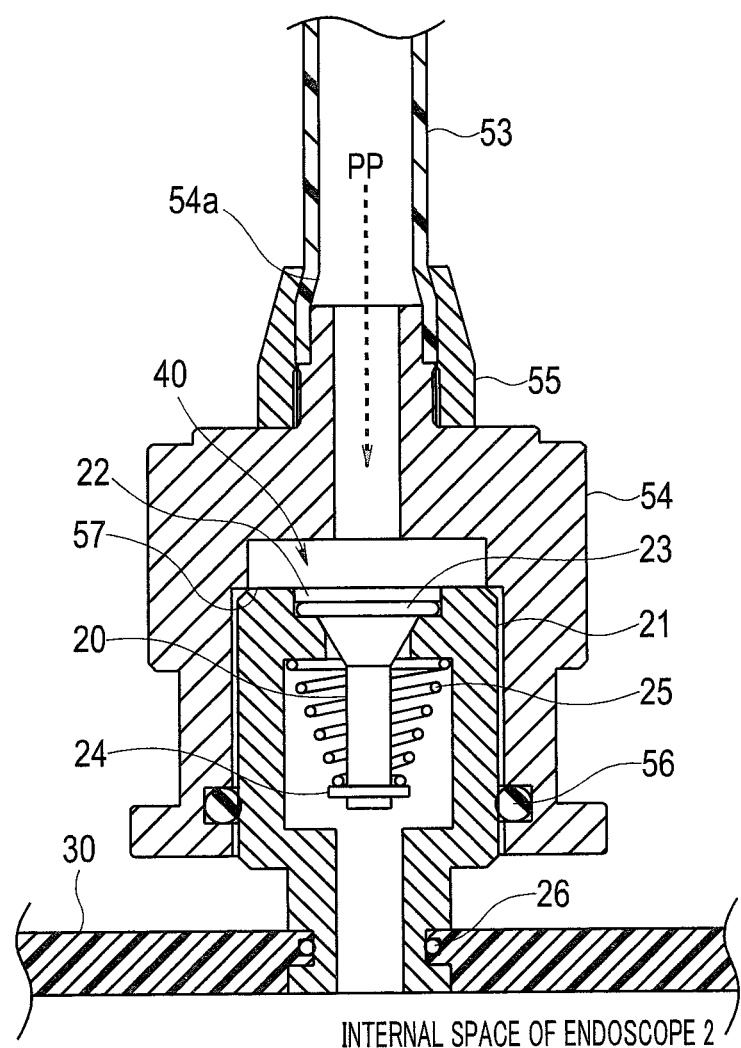
FIG. 9 is a sectional view illustrating a state where the air pipe sleeve is connected to the leak detection pipe sleeve, and a positive pressure is applied.
Figure 10:
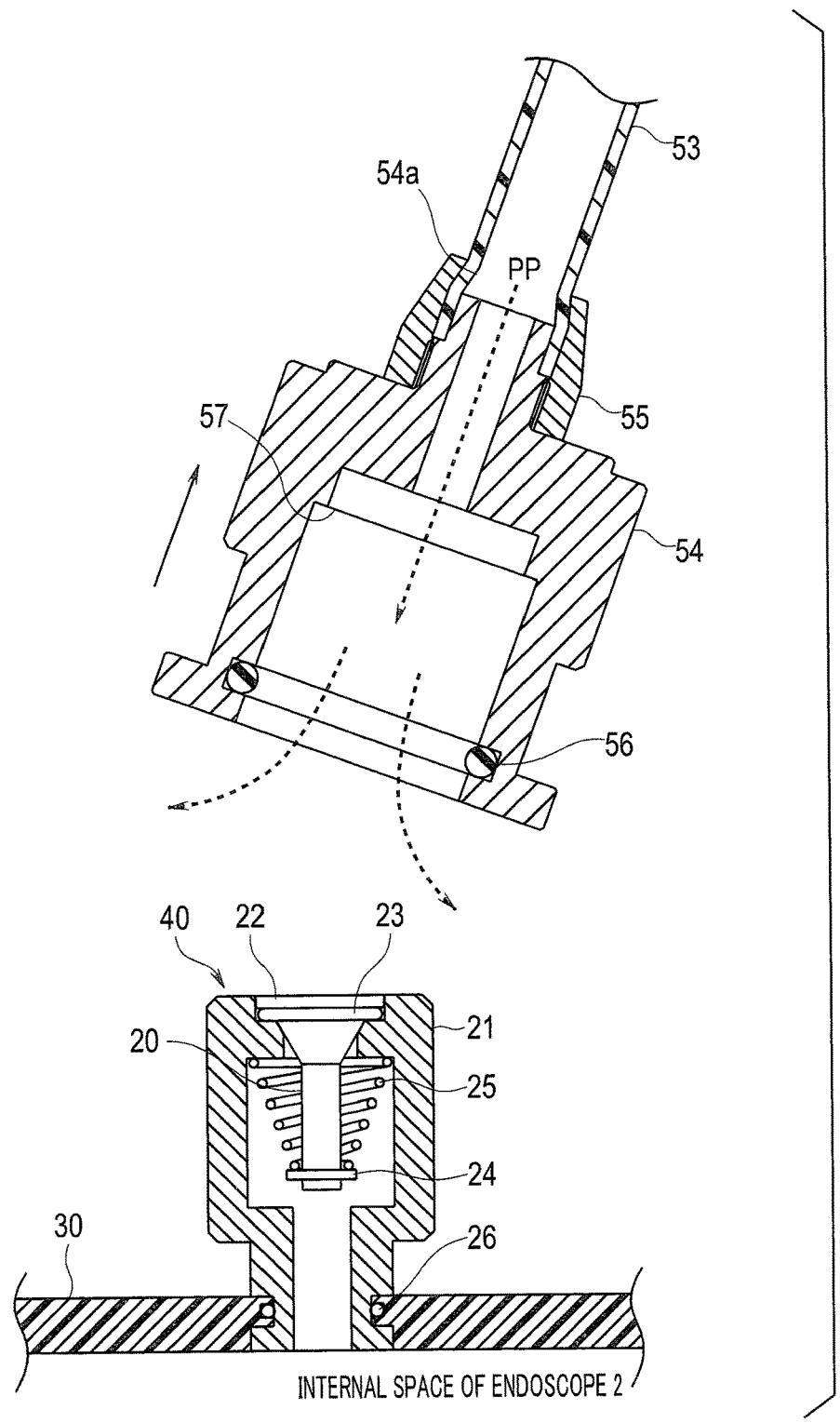
FIG. 10 is a sectional view illustrating a state where the air pipe sleeve comes off the leak detection pipe sleeve.
Figure 11:
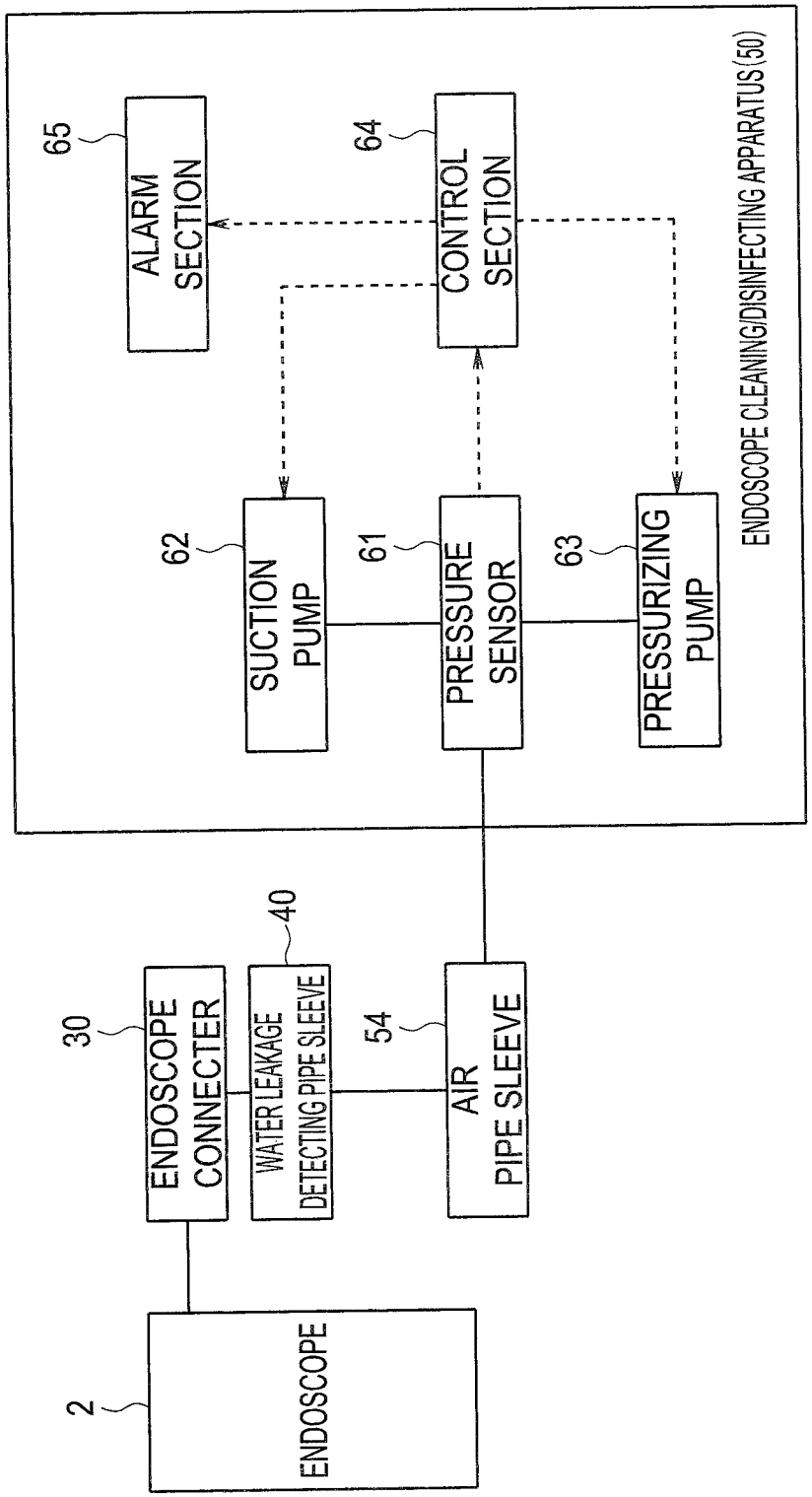
FIG. 11 is a block diagram illustrating internal configurations of the endoscope and the endoscope cleaning/disinfecting apparatus.

FIG. 1 is a general view illustrating a configuration of an endoscope apparatus. FIG. 2 is a perspective view illustrating an endoscope connector. FIG. 3 is a plan view illustrating a state where an endoscope is set in a sink of an endoscope cleaning/disinfecting apparatus. FIG. 4 is a sectional view illustrating configurations of a leak detection pipe sleeve and an air pipe sleeve. FIG. 5 is a perspective view illustrating a state where the air pipe sleeve is being connected to the leak detection pipe sleeve. FIG. 6 is a perspective view illustrating a state where the air pipe sleeve is connected to the leak detection pipe sleeve. FIG. 7 is a sectional view illustrating the state where the air pipe sleeve is connected to the leak detection pipe sleeve. FIG. 8 is a sectional view illustrating a state where the air pipe sleeve is connected to the leak detection pipe sleeve, and a negative pressure is applied. FIG. 9 is a sectional view illustrating a state where the air pipe sleeve is connected to the leak detection pipe sleeve, and a positive pressure is applied. FIG. 10 is a sectional view illustrating a state where the air pipe sleeve comes off the leak detection pipe sleeve. FIG. 11 is a block diagram illustrating internal configurations of the endoscope and the endoscope cleaning/disinfecting apparatus.

First, the endoscope of the present embodiment will be described below.

As illustrated in FIG. 1, an endoscope apparatus 1 is configured to have an endoscope 2, a camera control unit (hereinafter, described as CCU) 3, for example, that is an external apparatus, and a monitor (not illustrated).

The CCU 3 of the present embodiment serves as both a light source apparatus containing a light source for supplying illumination light to the endoscope 2, and a video processor that performs various kinds of signal processing and the like of an image pickup device included by the endoscope 2. In the CCU 3, an air-feeding pump (not illustrated) that supplies air or the like to an air-feeding conduit is provided.

The endoscope 2 includes an insertion portion 5, an operation portion 6, and a universal cable 7. The insertion portion 5 is an elongated member of a long length that is inserted to an observation target site. The insertion portion 5 is configured by connecting a distal end portion 8, a bending portion 9, and a flexible tube portion 10.

The distal end portion 8 contains an illumination optical system including a light guide, and an image pickup optical system including an image pickup apparatus, and a suction port that serves as both a nozzle and a treatment instrument lead-out port is provided in a distal end face (all not illustrated).

The bending portion 9 is configured to be bendable in four directions of up, down, left and right, for example. The flexible tube portion 10 is a tubular member having a long length and flexibility.

The operation portion 6 includes a grasping portion 6a, and the grasping portion 6a is connected to a proximal end portion of the insertion portion 5. The operation portion 6 is provided with a bending operation portion 11, various switches 12, an air/water feeding button 13, a suction button 14 and the like.

The bending operation portion 11 includes a bending operation knob 11a for performing a bending operation of the bending portion 9, and a fixing lever 11b for fixing the bending operation knob 11a in a desired rotation position.

The switches 12 are, for example, observation mode changeover switches for performing changeover such as a release switch, and a freeze switch. Note that reference sign 6b denotes a treatment instrument insertion port.

The universal cable 7 is provided to extend from a side surface of the operation portion 6. An endoscope connector 30 illustrated in FIG. 2 is provided at an end portion of the universal cable 7.

Here, a configuration of the endoscope connector 30 will be described.

The endoscope connector 30 in the present embodiment has a signal transmission cable 33 provided to extend from a side portion, as illustrated in FIG. 2. An electric connector 34 in FIG. 1 is provided at the other end side of the signal transmission cable 33.

In the endoscope connector 30, a light guide sleeve 35 and an air feeding pipe sleeve 36 that is an external connection section are provided to protrude from a proximal end face.

In the endoscope connector 30, a suction pipe sleeve 37, a water feeding pipe sleeve 38 and a pressurization pipe sleeve 39 that are external connection portions are provided on a surface of an exterior body.

Note that reference sign 40 denotes a leak detection pipe sleeve, reference sign 41 denotes an earth terminal, reference sign 42 denotes a universal cable bend prevention, reference sign 43 denotes a signal transmission cable bend prevention, and reference sign 44 denotes a tag containing convex portion. Inside the tag containing convex portion 44, an individual identification information chip such as a RFID chip is contained.

The endoscope 2 after use is cleaned and disinfected by the endoscope cleaning/disinfecting apparatus 50 as illustrated in FIG. 3.

More specifically, the endoscope 2 is set in an inside of a sink 51 of the endoscope cleaning/disinfecting apparatus 50 by a user. At this time, the user connects a cleaning/disinfecting tube 52 in the sink 51, which is connected to the endoscope cleaning/disinfecting apparatus 50, to the treatment instrument insertion port 6b or the like of the endoscope 2, and connects an air tube 53 to the leak detection pipe sleeve 40.

The endoscope cleaning/disinfecting apparatus 50 executes cleaning/disinfecting processing when a lid that covers the sink 51 in which the endoscope 2 is set is closed, the power supply is turned on, and a start button or the like is pressed.

Note that a detailed configuration of the endoscope cleaning/disinfecting apparatus 50 and the cleaning/disinfecting processing of the endoscope 2 are well-known, and therefore explanation of the configuration of the endoscope cleaning/disinfecting apparatus 50 and the cleaning/disinfecting processing will be omitted.

Note that an endoscope system 60 of the present embodiment is configured by the endoscope 2 and the endoscope cleaning/disinfecting apparatus 50.

Here, explanation will be made for the leak detection pipe sleeve 40 as a first pipe sleeve which is a main part of the present embodiment, and an air pipe sleeve 54 as a second pipe sleeve that is placed at an extension end of the air tube 53 which is connected to the leak detection pipe sleeve 40.

As illustrated in FIG. 4, the air pipe sleeve 54 is an annular member formed of a rigid resin, a metal or the like. In the air pipe sleeve 54, the air tube 53 is connected to a tube connection portion 54a, and a presser tube 55 for holding the air tube 53 so that the air tube 53 does not come off is screwed onto the tube connection portion 54a.

In the air pipe sleeve 54, a seal member 56 such as an O-shaped ring that keeps air tightness by closely contacting an outer circumferential portion of the leak detection pipe sleeve 40 is provided in an inner circumferential portion. Further, in an internal space of the air pipe sleeve 54, a step portion 57 that abuts on an upper end surface of the leak detection pipe sleeve 40 is formed.

The leak detection pipe sleeve 40 has a so-called check valve in which a valve body 20 is provided in an annular valve case 21 that is formed of a metal or the like.

The valve body 20 has an upper plate portion 22 in an outward flange shape in an upper end portion, and a valve rubber 23 such as an O-shaped ring is provided on an inner side of the valve case 21 to abut on the upper plate portion 22. The valve body 20 has a spring holder 24 in an outward flange shape in a lower end portion.

A spring 25 is placed to urge the valve body 20 to a lower side so that a lower end abuts on the spring holder 24. The spring 25 in this case has an inverted conical shape, and is placed so that an upper end abuts on a top surface of an inside of the valve case 21. Note that the spring 25 does not always have to be in the inverted conical shape if only the upper end abuts on the top surface of the inside of the valve case 21.

In other words, the leak detection pipe sleeve 40 is in an airtightly closed state with the valve rubber 23 in close contact with the upper opening portion of the valve case 21 by the valve body 20 receiving the urging force to a lower side from the spring 25 in a normal time. In the leak detection pipe sleeve 40, a seal member 26 such as an O-shaped ring that keeps air tightness is placed in a connection portion with the endoscope connector 30.

The leak detection pipe sleeve 40 and the air pipe sleeve 54 which are configured as above are connected as illustrated in FIG. 6 and FIG. 7 from states illustrated in FIG. 4 and FIG. 5. In other words, the air pipe sleeve 54 is fitted on the leak detection pipe sleeve 40 so as to cover the leak detection pipe sleeve 40.

When a power supply of the endoscope cleaning/disinfecting apparatus 50 is turned on in the state where the endoscope 2 is set in the sink 51 of the endoscope cleaning/disinfecting apparatus 50, and a start button or the like is pressed, leak detection processing is performed before cleaning/disinfecting processing.

In other words, in the conventional endoscope cleaning/disinfecting apparatus 50, leak detection processing is performed by soaking the endoscope 2 which is set in the sink 51 into water, but in the endoscope cleaning/disinfecting apparatus 50 of the present embodiment, leak detection processing is performed without soaking the endoscope 2 into water.

In the leak detection processing, a negative pressure (suction) is applied to the endoscope 2 first via the air tube 53 by the endoscope cleaning/disinfecting apparatus 50. Thereupon, by suction of air, the upper end surface of the leak detection pipe sleeve 40 abuts on the step portion 57 of the air pipe sleeve 54.

The seal member 56 which is provided inside of the air pipe sleeve 54 is in close contact with the outer circumferential surface of the valve case 21 of the leak detection pipe sleeve 40, and therefore, the air pipe sleeve 54 and the leak detection pipe sleeve 40 are brought into a state where the air pipe sleeve 54 and the leak detection pipe sleeve 40 are airtightly connected.

In the state where the negative pressure is applied to the inside of the endoscope 2 by the endoscope cleaning/disinfecting apparatus 50 in this way, the pressure is reduced in the air tube 53 more than in the endoscope 2. Therefore, as illustrated in FIG. 8, the valve body 20 of the leak detection pipe sleeve 4 opens. In other words, the valve body 20 moves to an upper side against the urging force of the spring 25.

Thereby, in the leak detection pipe sleeve 40, the valve rubber 23 which is in close contact with the upper opening portion of the valve case 21 separates from the upper opening portion, and a gap occurs. Thereby, air in the endoscope 2 is sucked into the air tube 53 at an endoscope cleaning/disinfecting apparatus 50 side (a dotted line NP in FIG. 8).

When the negative pressure processing is executed for a predetermined time period, and an internal pressure is stable at a fixed internal pressure (steady pressure), it can be detected that no hole (leak) occurs in the flexible tube portion 10, the outer sheath portion of the bending portion 9, the internal conduit and the like of the endoscope 2.

When the negative pressure processing is executed for the predetermined time period, and the internal pressure is not stabilized to the fixed internal pressure (steady pressure), it can be detected that a hole (leak) occurs in the flexible tube portion 10, the outer sheath portion of the bending portion 9, the internal conduit or the like of the endoscope 2. In this case, repair of the endoscope 2 is required.

Note that as for the leak detection processing, as another leak detection method, when the negative pressure processing is executed for a predetermined time period, and the internal pressure is lower than a predetermined threshold, it can also be detected that no hole (leak) occurs in the flexible tube portion 10, the outer sheath portion of the bending portion 9, the internal conduit or the like, because the negative pressure processing is sufficient.

When the negative pressure processing is executed for the predetermined time period, and the internal pressure is higher than the predetermined threshold, it can be detected that a hole (leak) occurs to the flexible tube portion 10, the outer sheath portion of the bending portion 9, the internal conduit or the like of the endoscope 2 because the negative pressure processing is not sufficient, and repair of the endoscope 2 is required.

In other words, in this case, it is detected that a hole (leak) does not occur when the detected pressure is a pressure that does not exceed the predetermined threshold, and it is detected that the hole (leak) occurs when the detected pressure is a pressure that exceeds the predetermined threshold.

Note that when the leak detection result of the endoscope 2 is normal, the endoscope cleaning/disinfecting apparatus 50 applies a positive pressure to (pressurizes) the endoscope 2 via the air tube 53 next. Thereupon, as illustrated in FIG. 9, the valve body 20 of the leak detection pipe sleeve 40 closes by pressurization by air. In other words, the valve body 20 moves to a lower side by the urging force of the spring 25.

Thereby, in the leak detection pipe sleeve 40, the valve rubber 23 closely contacts the upper opening portion of the valve case 21 and the inside of the endoscope 2 is brought into an airtight state. When the endoscope cleaning/disinfecting apparatus 50 directly applies a positive pressure (a dotted line PP in FIG. 9) via the air tube 53, the pressure in the air pipe sleeve 54 increases, and when the pressure exceeds a holding force by the seal member 56 of the air pipe sleeve 54, the air pipe sleeve 54 comes off the leak detection pipe sleeve 40 as illustrated in FIG. 10.

The endoscope cleaning/disinfecting apparatus 50 ends the leak detection processing due to pressure reduction, and subsequently executes the cleaning/disinfecting processing of the endoscope 2.

Note that as illustrated in FIG. 11, the endoscope cleaning/disinfecting apparatus 50 has a pressure sensor 61 inside that detects a pressure at a time of applying a negative pressure or a positive pressure to the endoscope 2. A suction pump 62 that is an air pump for applying a negative pressure, and a pressurizing pump 63 that is an air pump for applying a positive pressure are provided in the endoscope cleaning/disinfecting apparatus 50.

The pressure sensor 61, the suction pump 62 and the pressurizing pump 63 exchange signals with a control section 64 in the endoscope cleaning/disinfecting apparatus 50, a detection signal is inputted to the control section 64 from the pressure sensor 61, and a drive signal is outputted to the suction pump 62 and the pressurizing pump 63 from the control section 64.

The endoscope cleaning/disinfecting apparatus 50 includes an alarm section 65 for notifying the user of occurrence of a hole (leak) in the endoscope 2 when the hole (leak) occurs to the endoscope 2.

If the control section 64 determines that a hole (leak) occurs to the endoscope 2, the control section 64 outputs a control signal to the alarm section 65. Note that the alarm section 65 is configured to warn by a warning lamp, a warning sound, or character display on a liquid crystal monitor or the like. Note that the suction pump 62 and the pressurizing pump 63 may be combined into one air pump, and may be configured to switch a negative pressure and a positive pressure.

The endoscope system 60 of the present embodiment which is configured as above is configured to firstly apply negative pressure to the endoscope 2 and perform leak detection processing when the endoscope 2 is cleaned and disinfected by the endoscope cleaning/disinfecting apparatus 50, and to apply a positive pressure to the endoscope 2 and make the air pipe sleeve 54 come off the detection pipe sleeve 40 when there is no leak in the endoscope 2.

Thereby, in the endoscope system 60, the leak detection pipe sleeve 40 is in an exposed state in the cleaning/disinfecting processing which is executed after the leak detection processing, and the outer surface of the leak detection pipe sleeve 40 is also cleaned and disinfected by a cleaning solution and an antiseptic solution.

As a result, it is not necessary to remove the air pipe sleeve 54 from the leak detection pipe sleeve 40 of the endoscope 2 after cleaning and disinfection by the endoscope cleaning/disinfecting apparatus 50, the outer surface of the leak detection pipe sleeve 40 is also cleaned and disinfected by the cleaning/disinfecting processing of the endoscope cleaning/disinfecting apparatus 50, and time and effort of the user can be reduced.

The leak detection pipe sleeve 40 of the endoscope 2 has a simple structure in which a so-called check-valve is provided, and is easily reduced in size and can be produced at low cost, so that manufacture cost of the endoscope 2 can be reduced.

From the above explanation, the endoscope system 60 of the present embodiment is configured also to enable cleaning and disinfecting of the outer surface of the leak detection pipe sleeve of the endoscope 2 by the endoscope cleaning/disinfecting apparatus 50, reduce the cleaning/disinfecting work of the user, and enable the structure of the leak detection pipe sleeve 40 to be simplified and downsized to reduce the manufacture cost.

(First Modification)

Figure 12:
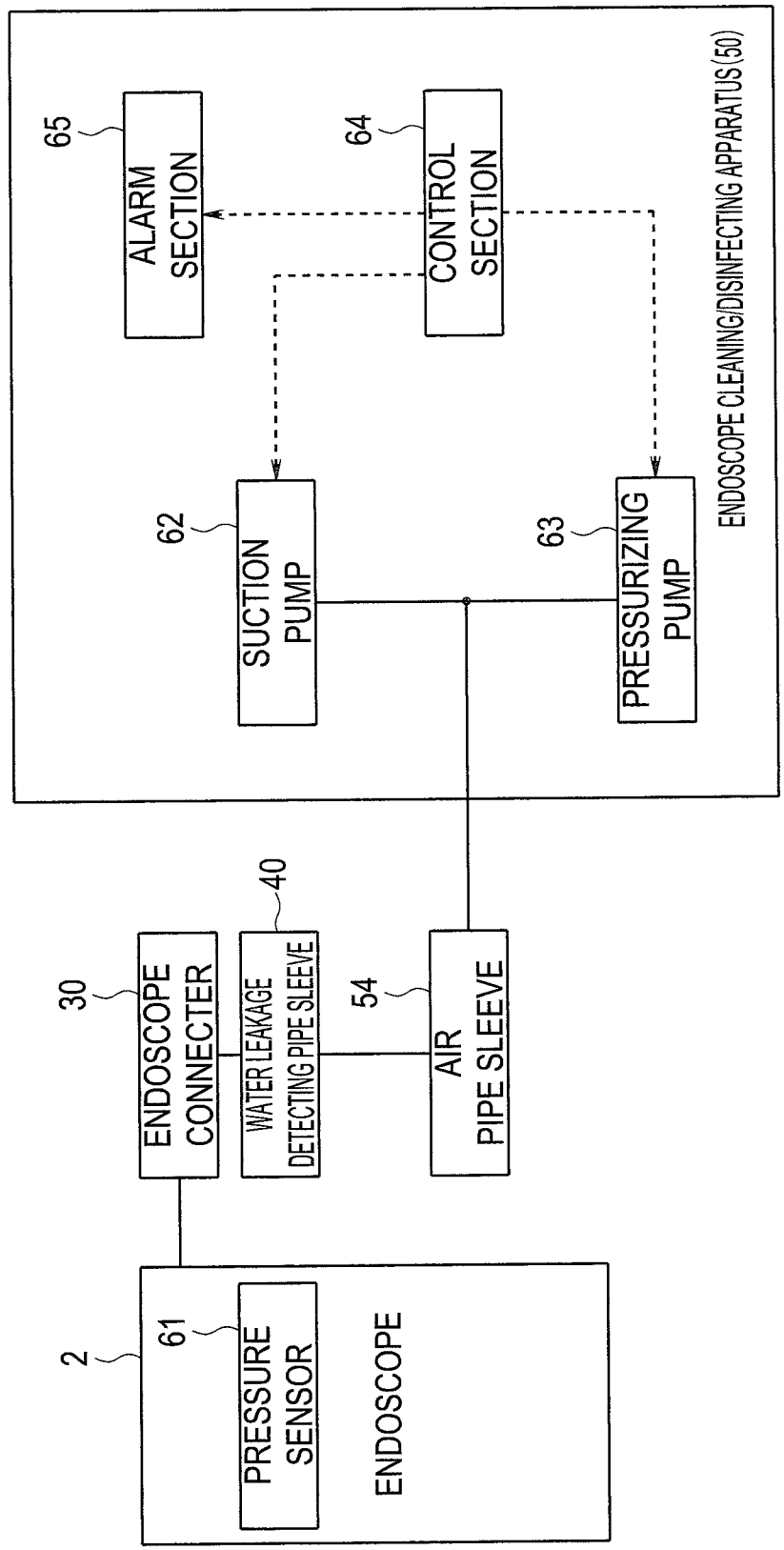
FIG. 12 is a block diagram illustrating an internal configuration of an endoscope and an endoscope cleaning/disinfecting apparatus of a first modification.

FIG. 12 is a block diagram illustrating internal configurations of an endoscope and an endoscope cleaning/disinfecting apparatus of a first modification.

As illustrated in FIG. 12, the pressure sensor 61 may be configured to be provided in the endoscope 2. In the case of the configuration, such a configuration can be adopted that a detection signal is outputted to the control section 64 by enabling wired communication or wireless communication with the control section 64 of the endoscope cleaning/disinfecting apparatus 50 to be performed.

Note that in each of the aforementioned embodiment and the present modification, the configuration of performing the leak detection processing of the endoscope 2 by the endoscope cleaning/disinfecting apparatus 50 is illustrated. However, the apparatus which performs leak detection processing may be a leak detection processing apparatus including the pressure sensor 61, the suction pump 62, the pressurizing pump 63, and the alarm section 65, or a configuration in which a function of performing leak detection processing is provided in each of an endoscope cleaning apparatus that performs only cleaning of the endoscope 2, and an endoscope disinfecting apparatus that performs only disinfection of the endoscope 2, without being limited to the above configuration.

(Second Modification)

Figure 13:
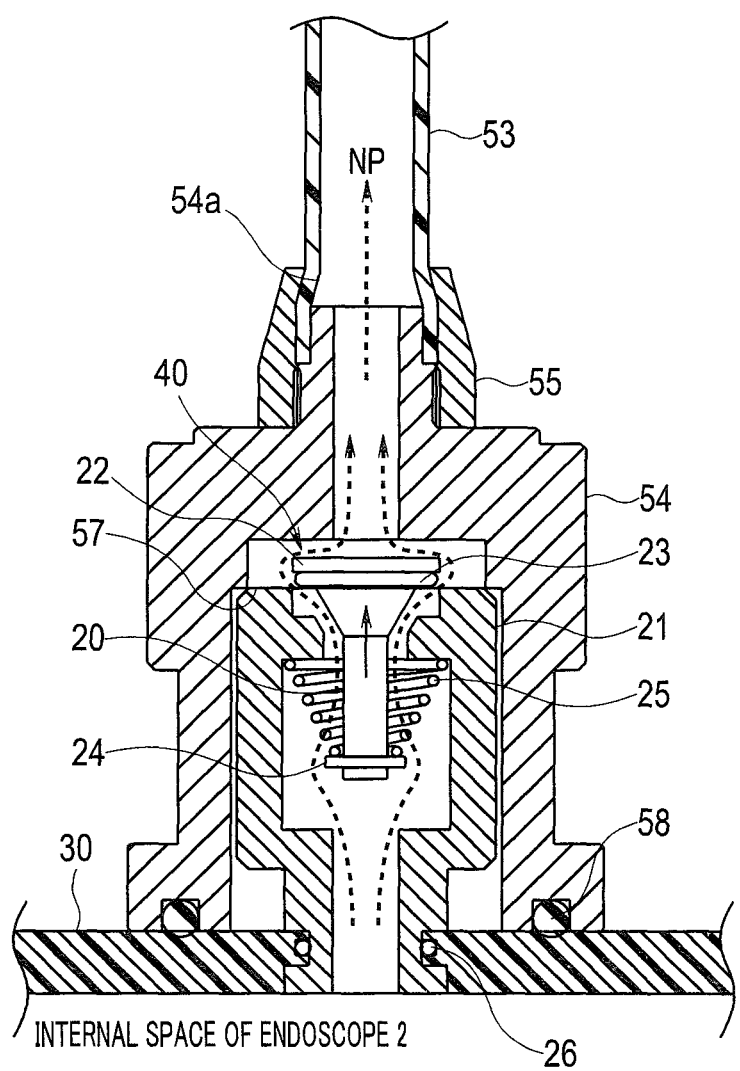
FIG. 13 is a sectional view illustrating a state where an air pipe sleeve is connected to a leak detection pipe sleeve of a second modification.

FIG. 13 is a sectional view illustrating a state where an air pipe sleeve is connected to a leak detection pipe sleeve of a second modification.

As illustrated in FIG. 13, a configuration may be adopted, in which a dimension in a long axis direction of the air pipe sleeve 54 is increased, a seal member 58 such as an O-shaped ring is provided on an end surface at an opening side, and the seal member 58 directly contacts the outer surface of the endoscope connector 30 closely when a negative pressure is applied.

(Third Modification)

Figure 14:
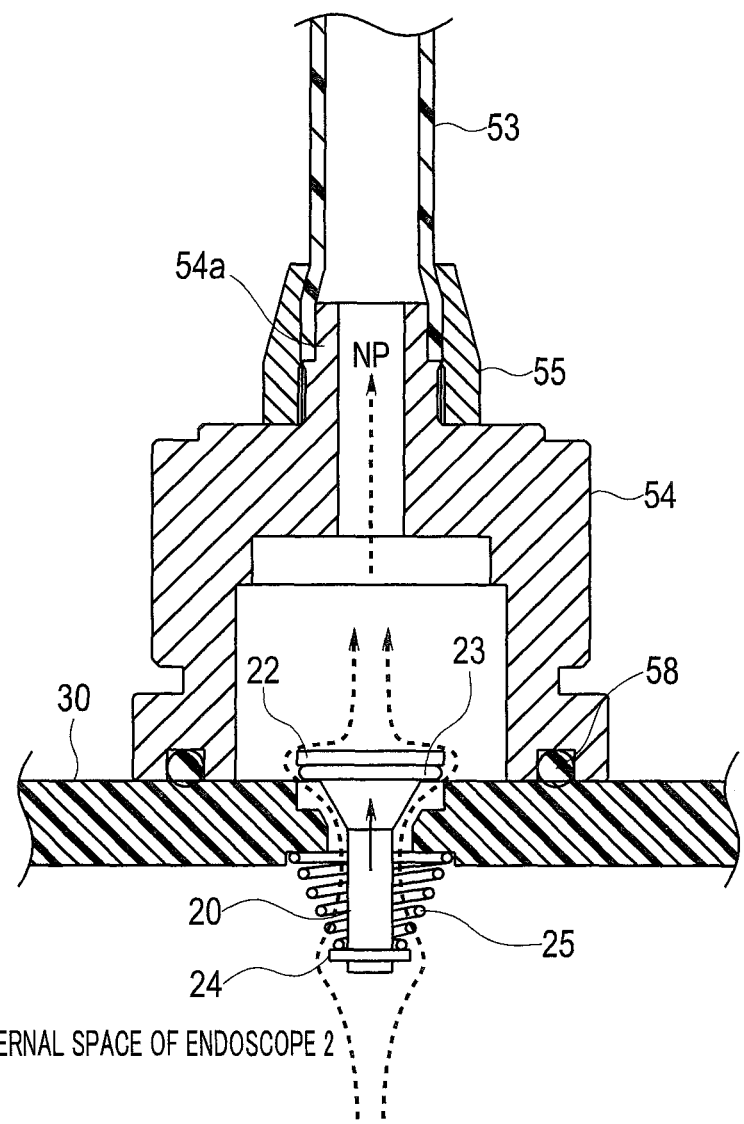
FIG. 14 is a sectional view illustrating a state where an air pipe sleeve is connected to a leak detection pipe sleeve of a third modification.

FIG. 14 is a sectional view illustrating a state where an air pipe sleeve is connected to a leak detection sleeve of a third modification.

As illustrated in FIG. 14, with a configuration of the air pipe sleeve 54 of the third modification, a configuration in which the valve body 20 is provided in an exterior surface portion of the endoscope connector 30 may be adopted.

The invention described in the above embodiment is not limited to the mode, and besides, it is possible to carry out various modifications within the range without departing from the gist of the invention in the stage of being carried out. Further, the above described mode includes the inventions in various stages, and various inventions can be extracted by arbitrary combinations in the plurality of components which are disclosed.

For example, even if some components are deleted from all the components shown in the mode, the configuration from which the components are deleted can be extracted as the invention when the problem which is described can be solved, and the effects which are described can be obtained.

According to the present invention, the endoscope system and the leak detection processing method for an endoscope can be realized, which also enable cleaning and disinfection of the outer surface of the leak detection pipe sleeve of the endoscope by the endoscope cleaning/disinfecting apparatus, reduce the cleaning/disinfecting work of the user, and can simplify and downsize the structure of the leak detection pipe sleeve and reduce the manufacture cost.

What is claimed is:

1. A leak detection processing apparatus comprising:
   one or more pumps configured to:
      be removably connected, via a pipe sleeve, to an internal space of an endoscope;
      apply negative pressure by air suction while connected to the internal space of the endoscope; and
      apply positive pressure by air feeding to disconnect the pipe sleeve from the endoscope;
   a pressure sensor configured to:
      detect a pressure in the internal space of the endoscope while the one or more pumps are connected to the internal space of the endoscope; and
      during or after application of the negative pressure by the one or more pumps, output a first detection signal indicating that a leak into the internal space of the endoscope has not occurred; and
   a controller configured to:
      control the one or more pumps to apply the negative pressure;
      receive the first detection signal; and
      control the one or more pumps to apply the positive pressure to disconnect the pipe sleeve from the endoscope.

2. The leak detection processing apparatus according to claim 1,
   wherein the pressure sensor is configured to:
      detect a pressure in the internal space of the endoscope while the one or more pumps apply the positive pressure, and
      during application of the positive pressure, output a second detection signal indicating that a pressure change is detected, and
   wherein the controller is configured to, in response to receiving the second detection signal, control the one or more pumps to stop application of the positive pressure.

3. The leak detection processing apparatus according to claim 1, further comprising:
   an endoscope cleaning/disinfecting apparatus configured to clean and disinfect the endoscope after leak detection processing of detecting the leak into the internal space of the endoscope has not occurred.

4. The leak detection processing apparatus according to claim 1,
   wherein the pressure sensor is configured to, during or after application of the negative pressure, output a third detection signal indicating that the pressure of the internal space of the endoscope is not fixed, and
   wherein the controller is configured to, in response to the third detection signal, control a warning section to output a warning.

5. The leak detection processing apparatus according to claim 1,
   wherein the pressure sensor is configured to, during or after application of the negative pressure, output a fourth detection signal indicating that the pressure of the internal space of the endoscope exceeds a predetermined threshold,
   wherein the controller is configured to, in response to the fourth detection signal, control a warning section to output a warning.

6. The leak detection processing apparatus according to claim 1,
   wherein the one or more pumps comprise:
      a suction pump configured to apply the negative pressure; and
      a pressurizing pump configured to apply the positive pressure.

7. The leak detection processing apparatus according to claim 1, further comprising:
   the pipe sleeve configured to connect the endoscope to the one or more pumps, and to be disconnected from the endoscope in response to application of the positive pressure by the one or more pumps.

8. The leak detection processing apparatus according to claim 7, further comprising:
   a seal provided to an inner surface of the pipe sleeve.

9. The leak detection processing apparatus according to claim 8,
   wherein the seal is configured to contact the endoscope when the pipe sleeve connects the endoscope to the one or more pumps.

* * * * *